United States Patent
Onogi et al.

(10) Patent No.: US 9,297,778 B2
(45) Date of Patent: Mar. 29, 2016

(54) SENSOR CONTROL APPARATUS, SENSOR CONTROL SYSTEM, AND SENSOR CONTROL METHOD

(75) Inventors: Hirotaka Onogi, Kakamigahara (JP); Kenji Kato, Nagoya (JP); Satoshi Teramoto, Nisshin (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 1034 days.

(21) Appl. No.: 13/418,903

(22) Filed: Mar. 13, 2012

(65) Prior Publication Data

US 2012/0234697 A1 Sep. 20, 2012

(30) Foreign Application Priority Data

Mar. 14, 2011 (JP) .................................. 2011-54979

(51) Int. Cl.
*G01N 27/407* (2006.01)

(52) U.S. Cl.
CPC .................................. *G01N 27/4074* (2013.01)

(58) Field of Classification Search
CPC ............ G01N 27/404–27/407; G01N 27/409; G01N 27/419; G01N 27/41; G01N 27/4065; F02D 41/146; F02D 41/1494; F02D 41/1454
See application file for complete search history.

(56) References Cited

U.S. PATENT DOCUMENTS

| | | | | |
|---|---|---|---|---|
| 6,136,170 A | * | 10/2000 | Inoue et al. ................... | 204/424 |
| 2009/0164091 A1 | * | 6/2009 | Kobayashi et al. ........... | 701/102 |
| 2010/0140113 A1 | * | 6/2010 | Teramoto et al. ............. | 205/782 |

FOREIGN PATENT DOCUMENTS

JP 2010-156676 A 7/2010

* cited by examiner

*Primary Examiner* — J. Christopher Ball
*Assistant Examiner* — Maris R Kessel
(74) *Attorney, Agent, or Firm* — Sughrue Mion, PLLC

(57) ABSTRACT

A sensor control apparatus is disclosed, including a preliminary control for supplying a constant current to a second oxygen pump cell of a gas sensor for a constant period of time so as to control to a constant level the amount of oxygen pumped out from a second measurement chamber (S40 to S50). At the beginning of drive control (S55 to S80), oxygen is pumped back into the second measurement chamber. During the pumping back operation, an $NO_X$ concentration correspondence value has a large time course change and is not stable. The $NO_X$ concentration correspondence value is corrected using correction data common among gas sensors, wherein the timing for applying the correction data is adjusted by making use of an application time determined in accordance with individual differences of each gas sensor.

7 Claims, 6 Drawing Sheets

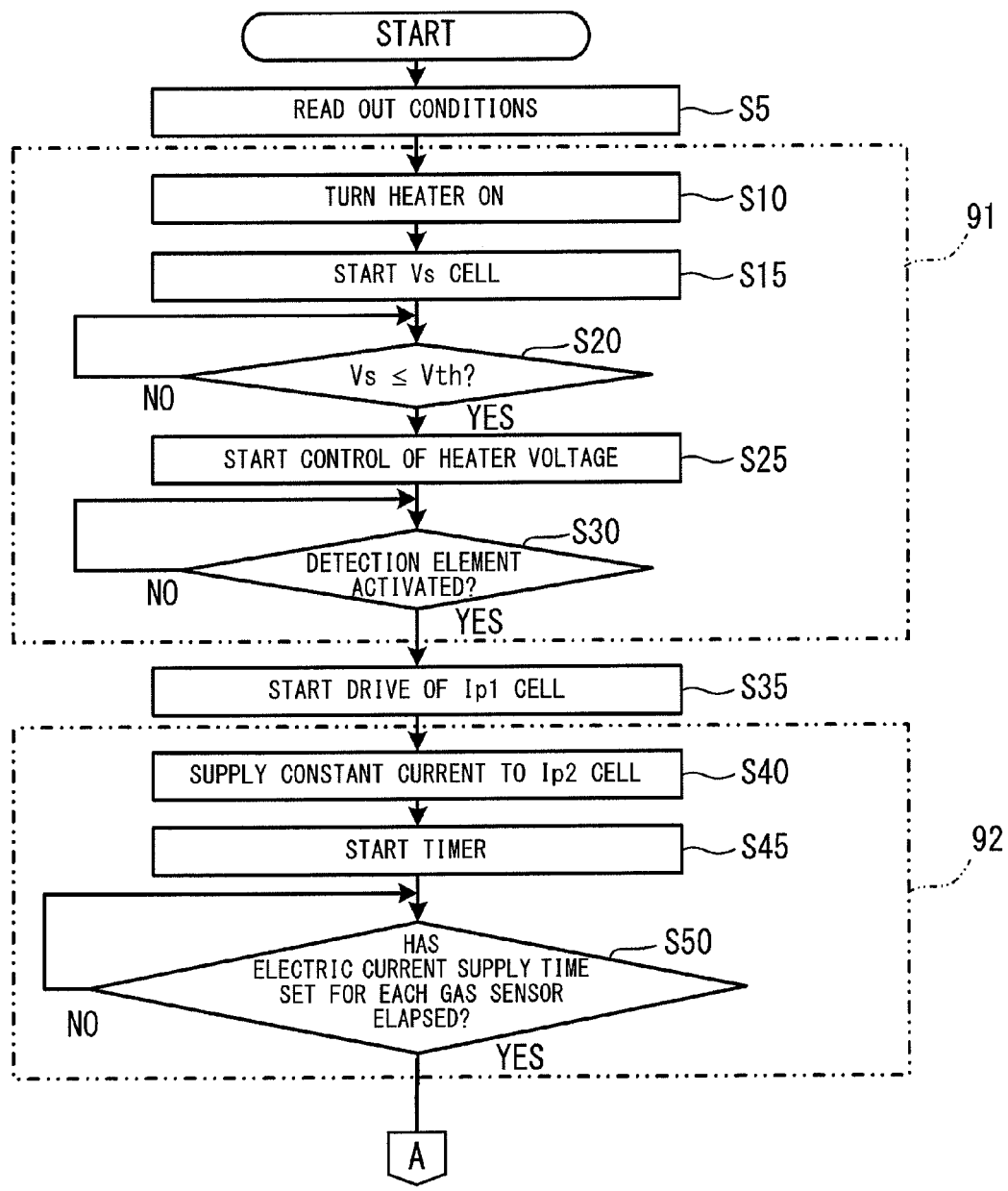

SENSOR CONTROL APPARATUS, SENSOR CONTROL SYSTEM, AND SENSOR CONTROL METHOD

BACKGROUND OF THE INVENTION

1. Field of the Invention

The present invention relates to a sensor control apparatus, a sensor control system, and a sensor control method adapted to calculate a concentration correspondence value that represents the concentration of a specific gas contained in a gas to be detected (hereinafter referred to as an "object gas").

2. Description of the Related Art

Conventionally, a gas sensor has been utilized which detects the concentration of a specific gas contained in an object gas such as exhaust gas. For example, an $NO_X$ sensor, which detects nitrogen oxides (hereinafter referred to as "$NO_X$") as a specific gas, includes a detection element which has an oxygen concentration detection cell, a first oxygen pump cell, and a second oxygen pump cell, each composed of an oxygen-ion conductive solid electrolyte layer and porous electrodes formed thereon. The first oxygen pump cell pumps oxygen out of a first measurement chamber into which an object gas is introduced, or pumps oxygen into the first measurement chamber. The second oxygen pump cell pumps oxygen out of a second measurement chamber that is in communication with the first measurement chamber.

A control apparatus for the $NO_X$ sensor supplies current to the first oxygen pump cell so as to pump oxygen out of the first measurement chamber or pump oxygen into the first measurement chamber such that the oxygen concentration detection cell facing the first measurement chamber outputs a constant voltage. Thus, the oxygen concentration of the object gas within the first measurement chamber is controlled to a constant level. Also, the control apparatus applies a constant voltage between the electrodes of the second oxygen pump cell so as to pump oxygen out of the gas introduced from the first measurement chamber into the second measurement chamber (the gas whose oxygen concentration has been adjusted by the first oxygen pump cell). As a result of applying the constant voltage, $NO_X$ within the gas is decomposed, and oxygen ions originating from the $NO_X$ flow through the second oxygen pump cell. The control apparatus detects the concentration of $NO_X$ within the object gas on the basis of the current flowing through the second oxygen pump cell.

In the case where the concentration of $NO_X$ contained in, for example, exhaust gas discharged from an internal combustion engine is detected by use of an $NO_X$ sensor, the gas present in the second measurement chamber approaches a lean state close to that of the atmosphere, with the passage of time from when the previous operation of the internal combustion engine has been stopped to restart thereof. In view of such a phenomenon, some control apparatuses are configured to perform, at the time of startup of the internal combustion engine, preliminary control so as to temporarily and rapidly pump oxygen out of the second measurement chamber. Since the preliminary control can lower the oxygen concentration within the second measurement chamber to a predetermined low oxygen concentration, at which the concentration of $NO_X$ can be detected and at an earlier timing as compared with the case where the preliminary control is not performed, the control apparatus can start detecting the $NO_X$ concentration at an earlier timing as compared to the case where preliminary control is not performed.

Also, the oxygen concentration within the second measurement chamber at the time when the preliminary control ends is lower than the predetermined low oxygen concentration at which the concentration of $NO_X$ can be detected. At the beginning of drive control for driving the detection element subsequent to preliminary control, oxygen is pumped back into the second measurement chamber such that the voltage applied to the second oxygen pump cell becomes the above-mentioned constant voltage. After the oxygen concentration within the second measurement chamber assumes the predetermined low oxygen concentration and the output of the detection element becomes stable, detection of the $NO_X$ concentration is performed.

Incidentally, it has been known that, when the voltage applied to the second oxygen pump cell is equal to or higher than a predetermined value, dissociation of moisture ($H_2O$) contained in the object gas occurs on an electrode of the second oxygen pump cell. It has also been known that, since oxygen ions generated as a result of dissociation of $H_2O$ flow between the electrodes of the second oxygen pump cell, the current flowing therethrough increases in accordance with the concentration of $H_2O$ contained in the object gas. In the case where a high voltage equal to or higher than the predetermined value is applied to the second oxygen pump cell during the preliminary control, even when the same detection element is used, the oxygen concentration within the second measurement chamber at the end of the preliminary control changes depending on the $H_2O$ concentration. Therefore, in a period during which oxygen is pumped back after the start of drive control, the output value of the detection element exhibits a time course change (a change with time), and the trend of the time course change (in other words, a change in the output value with time, or a curve (pattern) depicted on a graph which shows the relation between the output value of the detection element and elapse of time) changes depending on the $H_2O$ concentration.

A control apparatus which addresses the above-described problem has been known (for example, see Patent Document 1). The known control apparatus supplies current of a predetermined magnitude to the second oxygen pump cell for a certain period of time such that the amount of oxygen pumped out by the second oxygen pump cell becomes constant. When the control apparatus performs such control, the oxygen concentration within the second measurement chamber at the end of the preliminary control can be made substantially constant irrespective of the $H_2O$ concentration. Therefore, the trend of the time course change of the output value of the detection element in the period during which pumping back of oxygen is performed after the start of the drive control becomes constant irrespective of the $H_2O$ concentration, which enables the control apparatus to stably measure the $NO_X$ concentration.

[Patent Document 1] Japanese Patent Application Laid-Open (kokai) No. 2010-156676

3. Problems to be Solved by the Invention

However, even when the time course change exhibits a substantially constant trend at the beginning of the period during which oxygen is pumped back after the start of the drive control, the timing at which the output value of the detection element exhibits the trend of the time course change may deviate from an ideal timing because of individual differences among detection elements (variation among individual detection elements). The conventional control apparatus does not detect the concentration of $NO_X$ at the beginning of the drive control, waits for elapse of a predetermined time, and starts the detection of the $NO_X$ concentration after the output of the detection element becomes stable. Therefore, the above-mentioned deviation of the timing at which the output value of the detection element exhibits the trend of the time course change in the period during which oxygen is pumped back has not been taken into consideration.

SUMMARY OF THE INVENTION

The present invention has been accomplished so as to solve the above-described problem, and an object thereof is to provide a sensor control apparatus, a sensor control system, and a sensor control method which apply output correction in accordance with individual differences among detection elements at an earlier timing so as to start detection of concentration of a specific gas at the earlier timing.

In accordance with a first mode (1), the present invention provides a sensor control apparatus for controlling a gas sensor including a first measurement chamber into which an object gas is introduced, a first oxygen pump cell having a first solid electrolyte layer and paired first electrodes provided on the inside and outside, respectively, of the first measurement chamber, a second measurement chamber in communication with the first measurement chamber, and a second oxygen pump cell having a second solid electrolyte layer and paired second electrodes provided on the inside and outside, respectively, of the second measurement chamber. The sensor control apparatus comprises drive control means for performing drive control for adjusting an oxygen concentration of the object gas introduced into the first measurement chamber by supplying electric current to the first oxygen pump cell and for applying an operating voltage to the second oxygen pump cell; preliminary control means for performing, before start of the drive control, preliminary control which supplies a constant current to the second oxygen pump cell over a constant period of time, to thereby control to a constant level an amount of oxygen pumped out from the second measurement chamber to outside of the second measurement chamber; calculation means for calculating a concentration correspondence value which represents a concentration of a specific gas contained in the object gas, on the basis of the magnitude of current flowing through the second oxygen pump cell to which the operating voltage is applied after the start of the drive control; storage means for storing, as correction data common among a plurality of the gas sensors, pattern data which represents a pattern of a time course change in the concentration correspondence value after the drive control is started after the preliminary control which has been set in advance is executed, which pattern data is obtained under a condition where both the preliminary control and the drive control are performed in the presence of a reference gas having a known concentration; determination means for determining a timing for applying the correction data, such that a pattern of a time course change exhibited by the concentration correspondence value after the start of the drive control approximately coincides with the pattern of the time course change represented by the correction data; and correction means for correcting the concentration correspondence value by applying the correction data to the concentration correspondence value on the basis of the timing determined by the determination means.

The amount of oxygen pumped out by the second oxygen pump cell is in proportion to the current flowing between the paired second electrodes of the second oxygen pump cell. Therefore, in the sensor control apparatus of the first mode, at the end of the preliminary control, the oxygen concentration within the second measurement chamber becomes substantially the same level, irrespective of the concentration of $H_2O$ contained in the object gas, if the same individual gas sensor is used. Therefore, as a result of execution of the preliminary control, the time course change of the concentration correspondence value computed after the end of the preliminary control exhibits substantially the same pattern irrespective of the concentration of $H_2O$ contained in the object gas or the gas sensor that is used. Then, if the correction data is applied on the basis of the timing which is determined by the determination means in accordance with individual differences among the gas sensors, the concentration correspondence value in a period in which its time course change is large can be corrected such that the time course change is reduced. Therefore, the concentration correspondence value can be output at an earlier timing determined in accordance with individual differences among gas sensors.

In a preferred embodiment (2) of the first mode, the storage means may store an application time which is determined for the gas sensor on an individual basis and represents a time between the start of the drive control and the timing for applying the correction. The application time is used to apply the correction data such that the pattern of the time course change in the concentration correspondence value after the drive control is started after execution of the preliminary control, both controls being performed in the presence of the reference gas, approximately coincides with the pattern of the time course change represented by the correction data. The determination means may determine that the timing for applying the correction data has come when the application time elapses after the start of the drive control.

In the case where the timing for applying the correction data is obtained in advance, as an application time, in accordance with individual differences among the gas sensors, and the application timing is determined on the basis of elapse of the application time, the application timing need not be obtained through computation or the like. Therefore, the processing performed by the determination means can be simplified, and the load acting on the determination means can be reduced.

In another preferred embodiment (3) of the first mode (1) or in accordance with (2) above, the storage means may further store control conditions of the sensor control apparatus which are determined for the gas sensor on an individual basis and relate to adjustment of the amount of pumped out oxygen, the control conditions being determined such that the concentration correspondence value after the drive control is started after execution of the preliminary control, both controls being performed in the presence of the reference gas, falls within a target range. The preliminary control means may execute the preliminary control under the control conditions.

Since the control conditions which adjust the amount of oxygen pumped out at the time of execution of the preliminary control are individually determined for each gas sensor, the pattern of the time course change of the concentration correspondence value after the drive control is started in the presence of a reference gas having a known concentration falls within the target range. That is, since the control conditions which adjust the amount of oxygen pumped out at the time of execution of the preliminary control are set for each gas sensor individually, the sensor control apparatus can effectively bring the concentration correspondence value calculated after the start of the drive control into the target range, without being influenced by manufacture-related variations, etc., of the gas sensor.

The target range is properly determined in consideration of an allowable variation of the concentration correspondence value after the start of drive control. Accordingly, the sensor control apparatus of the first mode exhibits substantially the same pattern in terms of a time course change in the concentration correspondence value calculated after completing the preliminary control (in other words, after the start of the drive control), even when the H₂O concentration of the object gas varies among a plurality of times of startup of the sensor control apparatus, or even when the output characteristic varies among the gas sensors. Therefore, when the concentration correspondence value is corrected by applying the correction data common among a plurality of gas sensors having the same structure, the correction of the concentration correspondence value can be performed more accurately.

In a preferred embodiment (4) in accordance with (3) above, the control conditions may include at least one of constant current and constant time determined for each gas sensor. In this case, the sensor control apparatus can reduce variation in the concentration correspondence value after the start of drive control among the gas sensors by executing a simple control; i.e., controlling conditions (the constant current and/or the electric current supply time determined for each gas sensor) under which electric current is supplied to the second oxygen pump cell at the time of execution of the preliminary control. In the case where the control conditions are set in such a manner that a time (constant time) over which electric current is supplied to the second oxygen pump cell is commonly set among the plurality of gas sensors, and the value of the constant current is set for each gas sensor in consideration of the output characteristic, the sensor control apparatus of the first mode can make the time from startup to the execution of drive control substantially the same among the gas sensors.

In a second mode (5), the present invention provides a sensor control system comprising a gas sensor and a sensor control apparatus according to any one of (1) to (4) above, wherein the gas sensor is controlled by the sensor control apparatus. Since a gas sensor having an individual difference and a sensor control apparatus which is adapted to the gas sensor are provided as a sensor control system, the detection of the concentration of the specific gas can be started earlier. In addition, since the accuracy of the concentration correspondence value obtained in the sensor control apparatus is higher, the reliability of the sensor control system can be secured.

In a third mode (6), the present invention provides a sensor control method which is performed in a sensor control apparatus for controlling a gas sensor including a first measurement chamber into which an object gas is introduced, a first oxygen pump cell having a first solid electrolyte layer and paired first electrodes provided on an inside and outside, respectively, of the first measurement chamber, a second measurement chamber in communication with the first measurement chamber, and a second oxygen pump cell having a second solid electrolyte layer and paired second electrodes provided on an inside and outside, respectively, of the second measurement chamber. The sensor control method comprises a drive control step of performing drive control for adjusting an oxygen concentration of the object gas introduced into the first measurement chamber by supplying electric current to the first oxygen pump cell and for applying an operating voltage to the second oxygen pump cell; a preliminary control step of performing, before start of the drive control, preliminary control which supplies a constant current to the second oxygen pump cell over a constant period of time, to thereby control to a constant level an amount of oxygen pumped out from the second measurement chamber to the outside of the second measurement chamber; a calculation step of calculating a concentration correspondence value which represents a concentration of a specific gas contained in the object gas, on the basis of the magnitude of current flowing through the second oxygen pump cell to which the operating voltage is applied after the start of the drive control; a determination step of determining a timing for applying correction data, such that a pattern of a time course change exhibited by the concentration correspondence value after the start of the drive control approximately coincides with a pattern of a time course change represented by the correction data, the correction data being pattern data which is stored in storage means of the sensor control apparatus commonly among a plurality of the gas sensors and which represents a pattern of a time course change in the concentration correspondence value after the drive control is started after the preliminary control which has been set in advance is executed, which pattern data is obtained under a condition where both the preliminary control and the drive control are performed in the presence of a reference gas; and a correction step of correcting the concentration correspondence value by applying the correction data to the concentration correspondence value on the basis of the timing determined by the determination step.

In a preferred embodiment (7) of the third mode (6), the storage means may further store an application time which is individually determined for the gas sensor and represents a time between the start of the drive control and the timing for applying the correction data, the application time being used to apply the correction data such that the pattern of the time course change in the concentration correspondence value after the drive control is started after execution of the preliminary control, both controls being performed in the presence of the reference gas, approximately coincides with the pattern of the time course change represented by the correction data. The determination step may determine that the timing for applying the correction data has come when the application time elapses after the start of the drive control.

As a result of the gas sensor being controlled by the sensor control method of the third mode, a user can obtain advantageous effects similar to those provided by the sensor control apparatus of the first mode.

BRIEF DESCRIPTION OF THE DRAWINGS

FIGS. 2A and 2B are flowcharts of main processing.

DESCRIPTION OF REFERENCE NUMERALS

Figure 1:
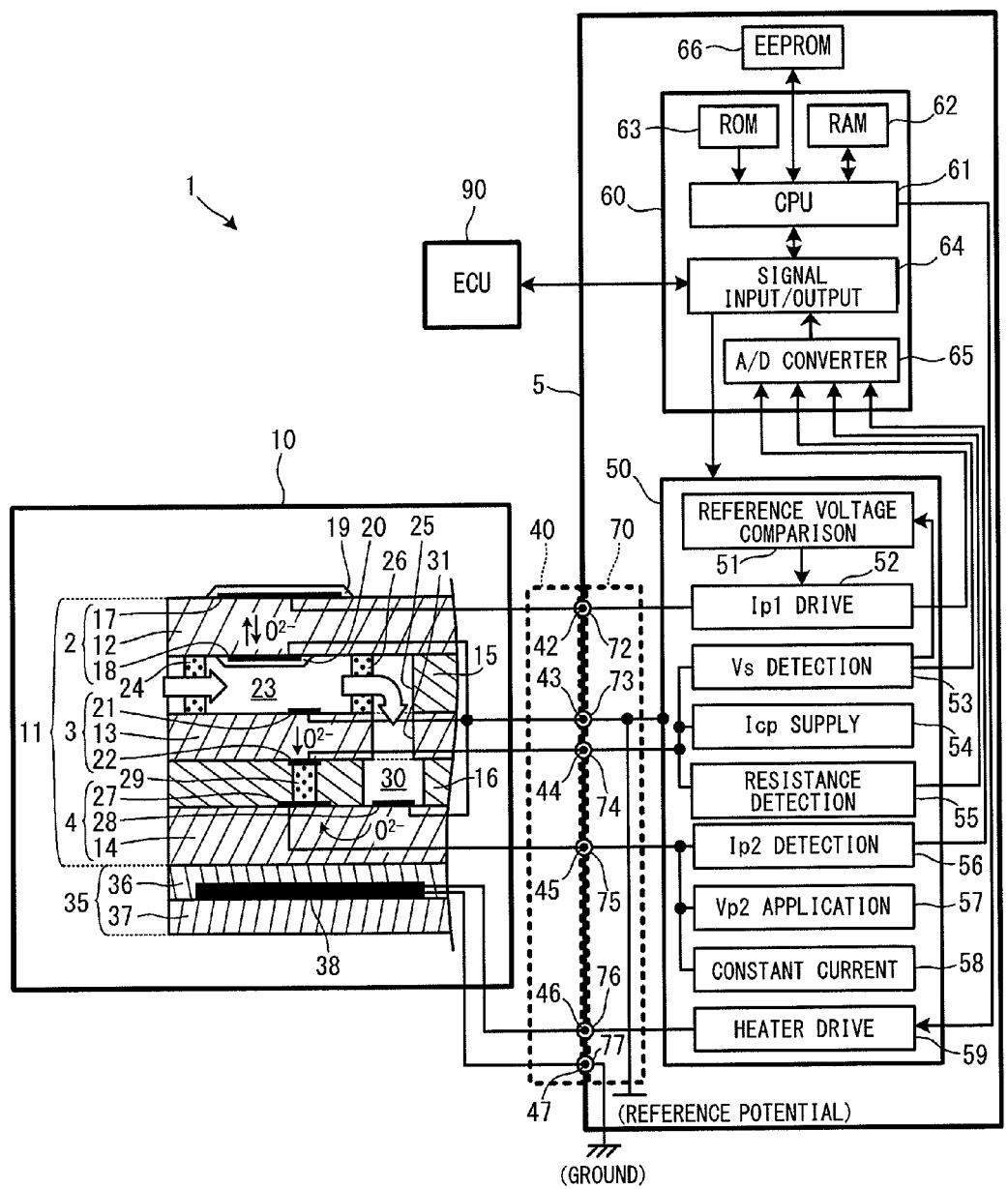
FIG. 1 is a conceptual diagram of a sensor control system 1 which includes a gas sensor 10 and a sensor control apparatus 5.

Reference numerals used to identify various features in the drawings including the following.
1: sensor control system
2: first oxygen pump cell
4: second oxygen pump cell
5: sensor control apparatus
10: gas sensor
12, 13, 14: solid electrolyte body
17, 18, 21, 22, 27, 28: electrode
23: first measurement chamber
30: second measurement chamber
60: microcomputer
61: CPU
63: ROM
66: EEPROM

DETAILED DESCRIPTION OF THE INVENTION

One embodiment common to a sensor control apparatus, a sensor control system, and a sensor control method according to the present invention will be described with reference to the drawings. Notably, the drawings which will be referred to are used only for the purpose of describing technical features which the present invention may employ, and the structure, etc., of an apparatus described therein are not intended to limit the present invention thereto and are mere explanatory examples.

A sensor control system 1 according to the present invention will be described with reference to FIG. 1. First, the outline of the function of the sensor control system 1 will be described. As shown in FIG. 1, the sensor control system 1 includes a gas sensor 10 and a sensor control apparatus 5. The sensor control apparatus 5 is electrically connected to the gas sensor 10, and has a function of detecting the concentration of nitrogen oxide ($NO_X$) (specific gas). The gas sensor 10 is attached to an exhaust passage (not shown) of an automobile, and outputs to the sensor control apparatus 5 a current value corresponding to the $NO_X$ concentration of exhaust gas. The sensor control apparatus 5 controls the gas sensor 10, and calculates, on the basis of the current value output from the gas sensor 10, a concentration correspondence value representing the $NO_X$ concentration of the exhaust gas (hereinafter referred to as an "$NO_X$ concentration correspondence value"). The sensor control apparatus 5 of the present embodiment calculates the $NO_X$ concentration as the $NO_X$ concentration correspondence value.

Next, the structure of the gas sensor 10, which is connected to the sensor control apparatus 5, will be described. The gas sensor 10 includes a detection element 11, a heater element 35, a connector section 40, and a housing (not shown). The detection element 11 has a layered structure formed by means of alternately laminating three plate-like solid electrolyte bodies 12, 13 and 14, and insulating members 15 and 16 formed of alumina or the like. The heater element 35 is laminated on the solid electrolyte body 14 so as to quickly activate the solid electrolyte bodies 12, 13 and 14 and stably maintain the activated states of the solid electrolyte bodies 12, 13 and 14. The connector section 40 is connected to the detection element 11 and the heater element 35 via lead wires, and is provided for establishing electrical connection between the gas sensor 10 and the sensor control apparatus 5. The housing holds the detection element 11 and the heater element 35 therein so as to attach the gas sensor 10 to the exhaust passage (not shown). Next, the structures of various sections of the gas sensor 10 will be described in detail.

First, the structure of the detection element 11 will be described. The detection element 11 includes a first measurement chamber 23, a second measurement chamber 30, a reference oxygen chamber 29, a first oxygen pump cell 2 (hereinafter referred to as the "Ip1 cell 2"), an oxygen partial pressure detection cell 3 (hereinafter referred to as the "Vs cell 3"), and a second oxygen pump cell 4 (hereinafter referred to as the "Ip2 cell 4").

The first measurement chamber 23 is a small space within the detection element 11 into which exhaust gas within the exhaust passage is first introduced. The first measurement chamber 23 is formed between the solid electrolyte body 12 and the solid electrolyte body 13. An electrode 18 is disposed on a wall surface of the first measurement chamber 23 formed by the solid electrolyte body 12, and an electrode 21 is disposed on a wall surface of the first measurement chamber 23 formed by the solid electrolyte body 13. A first porous diffusion resistor 24 is provided in the first measurement chamber 23 so as to be located on the front end side of the detection element 11. The first diffusion resistor 24 functions as a partition between the interior and exterior of the first measurement chamber 23, and limits the amount (per unit time) of the exhaust gas flowing into the first measurement chamber 23. Similarly, a second porous diffusion resistor 26 is provided in the first measurement chamber 23 so as to be located on the rear end side of the detection element 11. The second diffusion resistor 26 functions as a partition between the first measurement chamber 23 and the second measurement chamber 30, and limits the amount (per unit time) of the gas flowing from the first measurement chamber 23 into the second measurement chamber 30.

The second measurement chamber 30 is a small space surrounded by the solid electrolyte body 12, the second diffusion resistor 26, the wall surface of an opening 25, the wall surface of an opening 31 provided in the solid electrolyte body 13, the insulating member 16, and the solid electrolyte body 14. The second measurement chamber 30 communicates with the first measurement chamber 23. Exhaust gas whose oxygen concentration has been adjusted by the Ip1 cell 2 (hereinafter referred to as the "adjusted gas") is introduced into the second measurement chamber 30. An electrode 28 is disposed on a wall surface of the second measurement chamber 30 formed by the solid electrolyte body 14.

The reference oxygen chamber 29 is a small space surrounded by the insulating member 16, the solid electrolyte body 13, and the solid electrolyte body 14. A porous body formed of ceramic is placed in the reference oxygen chamber 29. An electrode 22 is disposed on a wall surface of the reference oxygen chamber 29 formed by the solid electrolyte body 13, and an electrode 27 is disposed on a wall surface of the reference oxygen chamber 29 formed by the solid electrolyte body 14.

The Ip1 cell 2 includes the solid electrolyte body 12, and an electrode 17 and the above-mentioned electrode 18, which are porous. The solid electrolyte body 12 is formed of, for example, zirconia, and has oxygen-ion conductivity. The electrodes 17 and 18 are provided on opposite sides of the solid electrolyte body 12 with respect to the lamination direction of the detection element 11. The electrodes 17 and 18 are formed of a material containing Pt as the main component. Examples of the material containing Pt as the main component include Pt, Pt alloy, and cermet containing Pt and ceramic. Moreover, porous protection layers 19 and 20 formed of ceramic are formed on the surfaces of the electrodes 17 and 18, respectively. When a current is applied between the two electrodes 17 and 18 of the Ip1 cell 2, the Ip1 cell 2 pumps oxygen (performs so-called oxygen pumping) between an atmosphere to which the electrode 17 is exposed (the atmosphere outside the detection element 11) and an atmosphere to which the electrode 18 is exposed (the atmosphere within the first measurement chamber 23).

The Vs cell 3 includes the solid electrolyte body 13, and the electrodes 21 and 22, which are porous. The solid electrolyte body 13 is formed of, for example, zirconia, and has oxygen-ion conductivity. The solid electrolyte body 13 is disposed to face the solid electrolyte body 12 with the insulating member 15 interposed therebetween. The electrodes 21 and 22 are provided on opposite sides of the solid electrolyte body 13 with respect to the lamination direction of the detection element 11. The electrode 21 is formed on the wall surface of the first measurement chamber 23 which faces the solid electrolyte body 12. The electrodes 21 and 22 are formed of the above-described material containing Pt as the main component. The Vs cell 3 generates an electromotive force mainly in accordance with a difference in oxygen partial pressure between atmospheres partitioned by the solid electrolyte body 13 (between the atmosphere within the first measurement chamber 23, to which the electrode 21 is exposed, and the atmosphere within the reference oxygen chamber 29, to which the electrode 22 is exposed).

The Ip2 cell 4 includes the solid electrolyte body 14, and the electrodes 27 and 28, which are porous. The solid electrolyte body 14 is formed of, for example, zirconia, and has oxygen-ion conductivity. The solid electrolyte body 14 is disposed to face the solid electrolyte body 13 with the insulating member 16 interposed therebetween. The electrodes 27 and 28, which are formed of the above-described material containing Pt as the main component, are provided on a surface of the solid electrolyte body 14 facing the solid electrolyte body 13. The Ip2 cell 4 pumps oxygen between atmospheres partitioned by the insulating member 16 (between the atmosphere within the reference oxygen chamber 29, to which the electrode 27 is exposed, and the atmosphere within the second measurement chamber 30, to which the electrode 28 is exposed).

Next, the heater element 35 will be described. The heater element 35 includes insulating layers 36 and 37, and a heater conductor 38. The insulating layers 36 and 37 are mainly formed of alumina and assume a sheet-like shape. The heater conductor 38 is a single conductor sandwiched between the insulating layers 36 and 37 and extending within the heater element 35. One end of the heater conductor 38 is grounded, and the other end of the heater conductor 38 is connected to a heater drive circuit 59. The heater conductor 38 is formed of a material containing Pt as the main component.

Next, the connector section 40 will be described. The connector section 40 is provided on the rear end side of the gas sensor 10, and includes terminals 42 to 47. The electrode 17 is electrically connected to the terminal 42 via a lead wire. The electrodes 18, 21 and 28 are electrically connected to the terminal 43 via lead wires so that the electrodes 18, 21 and 28 assume the same potential. The electrode 22 is electrically connected to the terminal 44 via a lead wire. The electrode 27 is electrically connected to the terminal 45 via a lead wire. The heater conductor 38 is electrically connected to the terminals 46 and 47 via lead wires.

Next, the electrical configuration of the sensor control apparatus 5 will be described. The sensor control apparatus 5 is an apparatus which controls the detection element 11 and the heater element 35 of the gas sensor 10. The sensor control apparatus 5 calculates an $NO_X$ concentration correspondence value on the basis of the current Ip2 obtained from the detection element 11, and outputs the calculated $NO_X$ concentration correspondence value to an ECU (electronic control unit) 90, which performs engine control, etc.

The sensor control apparatus 5 includes a drive circuit section 50, a microcomputer 60, and a connector section 70. The drive circuit section 50 controls the detection element 11 and the heater element 35. The microcomputer 60 controls the drive circuit section 50. The connector section 70 is electrically connected to the connector section 40 of the gas sensor 10. In the following, the configurations of various parts of the sensor control apparatus 5 will be described.

The drive circuit section 50 includes a reference voltage comparison circuit 51, an Ip1 drive circuit 52, a Vs detection circuit 53, an Icp supply circuit 54, a resistance detection circuit 55, an Ip2 detection circuit 56, a Vp2 application circuit 57, a constant current circuit 58, and a heater drive circuit 59. Next, the configurations of the various circuits provided in the drive circuit section 50 will be described in detail.

The Icp supply circuit 54 supplies a weak current Icp between the electrodes 21 and 22 of the Vs cell 3 so as to pump oxygen from the first measurement chamber 23 into the reference oxygen chamber 29. The Vs detection circuit 53 detects a voltage (electromotive force) Vs between the electrodes 21 and 22, and outputs the detected voltage to the reference voltage comparison circuit 51. The reference voltage comparison circuit 51 compares the voltage Vs detected by the Vs detection circuit 53 with a reference voltage (e.g., 425 mV), and outputs the results of the comparison to the Ip1 drive circuit 52.

The Ip1 drive circuit 52 supplies a current Ip1 between the electrodes 17 and 18 of the Ip1 cell 2. The Ip1 drive circuit 52 adjusts the magnitude and direction of the current Ip1 on the basis of the results of the comparison performed by the reference voltage comparison circuit 51 for the voltage Vs, such that the voltage Vs substantially coincides with a previously set reference voltage. As a result, the Ip1 cell 2 pumps oxygen out of the first measurement chamber 23 to the outside of the detection element 11, or pumps oxygen into the first measurement chamber 23 from the outside of the detection element 11. In other words, through electric current supply control performed by the Ip1 drive circuit 52, the Ip1 cell 2 adjusts the oxygen concentration within the first measurement chamber 23 such that the voltage Vs is maintained at a constant value (the value of the reference voltage).

The resistance detection circuit 55 periodically supplies a detection current to the Vs cell 3, and detects the internal resistance Rpvs of the Vs cell 3 on the basis of the amount of change in voltage (the amount of change in the voltage Vs) at that time. A value representing the amount of voltage change detected by the resistance detection circuit 55 is output to the microcomputer 60. The microcomputer 60 obtains the internal resistance Rpvs of the Vs cell 3. The internal resistance Rpvs of the Vs cell 3 has a correlation with the temperature of the Vs cell 3; that is, the temperature of the entire detection element 11. Therefore, the supply of electric current to the heater element 35 is controlled on the basis of the internal resistance Rpvs of the Vs cell 3.

The Ip2 detection circuit 56 detects a current Ip2 flowing from the electrode 28 to the electrode 27 of the Ip2 cell 4. The Vp2 application circuit 57 applies an operating voltage Vp2 (e.g., 450 mV, sufficient to dissociate $NO_X$) between the electrodes 27 and 28 of the Ip2 cell 4 when drive control processing to be described below is performed, and controls pumping of oxygen from the second measurement chamber 30 into the reference oxygen chamber 29. The constant current circuit 58 supplies a current Ip3 of a constant magnitude (e.g., 10 μA) between the electrodes 28 and 27 of the Ip2 cell 4 when preliminary control processing to be described later is performed.

The heater drive circuit 59 maintains the solid electrolyte bodies 12, 13 and 14 (the gas sensor 10) at a predetermined temperature. The heater drive circuit 59 is controlled by the microcomputer 60, and supplies a current to the heater conductor 38 of the heater element 35 to thereby heat the solid electrolyte bodies 12, 13 and 14 (in other words, the Ip1 cell 2, the Vs cell 3, and the Ip2 cell 4). On the basis of the above-described internal resistance Rpvs, the microcomputer 60 causes the heater drive circuit 59 to supply electric current to the heater conductor 38 through PWM (pulse width modulation) control such that the solid electrolyte bodies 12, 13 and 14 are heated to a target heating temperature.

The microcomputer 60 is a known computation unit including a CPU 61, ROM 63, RAM 62, a signal input/output section 64 and an A/D converter 65. In accordance with previously stored programs, the microcomputer 60 outputs control signals to the drive circuit section 50 to thereby control the operations of the various circuits provided in the drive circuit section 50. The ROM 63 stores various programs, and various parameters which are referred at the time of execution of the programs. The microcomputer 60 communicates with the ECU 90 via the signal input/output section 64. Also, the microcomputer 60 communicates with the drive circuit section 50 via the A/D converter 65 and the signal input/output section 64. Moreover, a well-known EEPROM 66 is connected to the microcomputer 60. The EEPROM 66 stores control conditions, application time, and correction time, described below. As described below, the EEPROM 66 also stores correction data for correcting the output of the gas sensor 10 by making use of a previously determined representative pattern 110.

The connector section 70 includes terminals 72 to 77. When the connector section 70 is connected to the connector section 40, the terminals 72 to 77 are connected to the terminals 42 to 47, respectively. The Ip1 drive circuit 52 is connected to the terminal 72 via wiring. The terminal 73 is connected to the reference potential of the sensor control apparatus 5 via wiring. The Vs detection circuit 53, the Icp supply circuit 54, and the resistance detection circuit 55 are connected to the terminal 74 via wiring. The Ip2 detection circuit 56, the Vp2 application circuit 57, and the constant current circuit 58 are connected to the terminal 75 via wiring. The heater drive circuit 59 is connected to the terminal 76 via wiring. The terminal 77 is grounded via wiring.

Next, operation of the sensor control apparatus 5 for detecting $NO_X$ concentration will be described. Exhaust gas flowing through the exhaust passage (not shown) is introduced into the first measurement chamber 23 via the first diffusion resistor 24. At that time, the Icp supply circuit 54 supplies a weak current Icp to the Vs cell 3 such that a current Icp flows from the electrode 22 to the electrode 21. Therefore, oxygen contained in the exhaust gas flows, in the form of oxygen ions, from the electrode 21 (negative electrode) into the solid electrolyte body 13, and then moves into the reference oxygen chamber 29. That is, as a result of supply of the current Icp between the electrodes 21 and 22, oxygen within the first measurement chamber 23 is fed into the reference oxygen chamber 29.

The Vs detection circuit 53 detects the voltage Vs between the electrodes 21 and 22. The reference voltage comparison circuit 51 compares the detected voltage Vs with a reference voltage (e.g., 425 mV), and outputs the comparison result to the Ip1 drive circuit 52. Here, when the oxygen concentration within the first measurement chamber 23 is adjusted such that the potential difference between the electrodes 21 and 22 becomes constant in the vicinity of the reference voltage, the oxygen concentration of the exhaust gas within the first measurement chamber 23 approaches a predetermined concentration C (e.g., 0.001 ppm).

Therefore, when the oxygen concentration of the exhaust gas introduced into the first measurement chamber 23 is lower than the concentration C, the Ip1 drive circuit 52 supplies the current Ip1 to the Ip1 cell 2 such that the electrode 17 serves as a negative electrode. As a result, the Ip1 cell 2 pumps oxygen from the outside of the detection element 11 into the first measurement chamber 23. Meanwhile, when the oxygen concentration of the exhaust gas introduced into the first measurement chamber 23 is higher than the concentration C, the Ip1 drive circuit 52 supplies the current Ip1 to the Ip1 cell 2 such that the electrode 18 serves as a negative electrode. As a result, the Ip1 cell 2 pumps oxygen out of the first measurement chamber 23 to the outside of the detection element 11. At that time, the oxygen concentration of the exhaust gas can be detected on the basis of the magnitude and flow direction of the current Ip1.

The adjusted gas; i.e., the exhaust gas whose oxygen concentration has been adjusted to the concentration C in the first measurement chamber 23, is introduced into the second measurement chamber 30 via the second diffusion resistor 26. $NO_X$ which is contained in the adjusted gas and which comes into contact with the electrode 28 within the second measurement chamber 30 is decomposed (reduced) into $N_2$ and $O_2$ by the catalytic action of the electrode 28. The oxygen produced as a result of the decomposition receives electrons from the electrode 28, to become oxygen ions (by dissociation), which flow through the solid electrolyte body 14 and move into the reference oxygen chamber 29. At that time, the value of the current Ip2 flowing between the paired electrodes 27 and 28 via the solid electrolyte body 14 corresponds to the $NO_X$ concentration, and the value of the current Ip2 is used for calculating the $NO_X$ concentration correspondence value.

Next, the main processing which is executed in the sensor control apparatus 5 in order to control the gas sensor 10 will be described with reference to FIGS. 2 to 8. The main processing shown in FIGS. 2A and 2B includes activation processing (processing within a two-dot chain line 91 in FIG. 2A), preliminary control processing (processing within a two-dot chain line 92 in FIG. 2A), and drive control processing (processing within a two-dot chain line 93 in FIG. 2B). The activation processing includes heating the detection element 11 by the heater element 35, to thereby activate the detection element 11. The control state of the sensor control apparatus 5 when the activation processing is being executed will be referred to as "activation control." The preliminary control processing includes pumping a predetermined amount of oxygen from the second measurement chamber 30 before the drive control processing is executed. The control state of the sensor control apparatus 5 when the preliminary control processing is being executed will be referred to as "preliminary control." The drive control processing is a process of adjusting, through supply of electric current to the Ip1 cell 2, the oxygen concentration of the exhaust gas introduced into the first measurement chamber 23, and applying the operating voltage Vp2 to the Ip2 cell 4. Furthermore, in the drive control processing, a process of calculating the $NO_X$ concentration correspondence value is executed on the basis of the magnitude of the current of the Ip2 cell 4 to which the operating voltage Vp2 is applied. The control state of the sensor control apparatus 5 when the drive control processing is being executed will be referred to as the "drive control."

Before describing the main processing in detail, the outline of correction which is performed in the sensor control system 1 of the present embodiment when the $NO_X$ concentration correspondence value is calculated will be described. The gas filling the second measurement chamber 30 at the time of startup of the gas sensor 10 becomes lean in a period between a point in time when operation of the internal combustion engine is stopped during the previous execution of the main processing (i.e., when the supply of exhaust gas is stopped) and a point in time when the gas sensor 10 is started. In the case where the preliminary control is not executed, immediately after the start of the drive control processing, the residual oxygen, etc., contained in the gas filling the second measurement chamber 30 before the start of that processing is pumped out from the second measurement chamber 30. In such a case, the current Ip2, which flows through the Ip2 cell 4, greatly changes in accordance with the residual oxygen, irrespective of the actual $NO_X$ concentration of the exhaust gas, which is to be calculated. Therefore, immediately after the start of the drive control processing, the $NO_X$ concentration correspondence value based on the current Ip2 does not correspond to the actual $NO_X$ concentration of the exhaust gas.

In order to solve such a problem, the sensor control apparatus 5 executes the preliminary control processing prior to the drive control processing, to thereby lower the oxygen concentration within the second measurement chamber 30 (in a lean atmosphere state). However, as described above, there is a problem that, in the case where a constant voltage equal to or greater than a predetermined level is applied to the Ip2 cell 4, the amount of oxygen pumped out by the Ip2 cell 4 changes depending on the concentration of $H_2O$ contained in the gas within the second measurement chamber 30. In view of the above, in the present embodiment, during the preliminary control, the constant current circuit 58 is operated, so that the current supplied to the Ip2 cell 4 becomes constant. With this operation, if the same gas sensor 10 is used, every time the preliminary control processing is performed, substantially the same amount of oxygen can be pumped out from the second measurement chamber 30. In the present embodiment, the constant current Ip3 to be supplied to the Ip2 cell 4 at the time of the preliminary control is set to 10 μA. At that time, the voltage applied to the Ip2 cell 4 is greater than the operating voltage Vp2 (425 mV), which is the voltage applied to the Ip2 cell 4 during the drive control. Therefore, the amount of oxygen pumped out per unit time during the preliminary control is greater than that during the drive control.

Moreover, as described above, a characteristic representing the relation between the $NO_X$ concentration and the $NO_X$ concentration correspondence value based on the current Ip2 (hereinafter referred to as the "output characteristic") may vary among gas sensors 10 even when they have the same structure. For example, due to manufacture-related variations, the output characteristic may vary among a plurality of gas sensors 10 even at the same $NO_X$ concentration. Therefore, a problem arises that, even when the concentration of $H_2O$ contained in exhaust gas is constant, the time required for the current Ip2 to become stable after the start of the drive control performed after the end of the preliminary control may vary among the gas sensors 10 in accordance with their output characteristics.

Therefore, if the same control conditions for the preliminary control are set for a plurality of gas sensors 10, the trend of a time course change in the $NO_X$ concentration correspondence value immediately after the start of the drive control (hereinafter referred to as a "change pattern") may vary among the gas sensors 10. In view of the above, in the present embodiment, the control conditions are set for each gas sensor 10 such that the $NO_X$ concentration correspondence value calculated after the start of the drive control processing (in other words, after the end of the preliminary control) falls within a target range (target concentration range). The control conditions refer to conditions associated with the amount of oxygen pumped out from the second measurement chamber 30 during execution of the preliminary control. For example, the control conditions include at least one of electric current supply time and the value of constant current at the time of execution of the preliminary control. In the sensor control apparatus 5 of the present embodiment, of the parameters associated with the amount of oxygen pumped out from the second measurement chamber 30, the electric current supply time over which the constant current (10 μA) is supplied to the Ip2 cell 4 (preliminary control execution time) is set for each individual gas sensor 10. As to the remaining parameters, common values are set for the different gas sensors 10.

The electric current supply time, which is contained in the control conditions for the preliminary control, is set for each individual gas sensor 10 in accordance with the following procedure, for example. For preparation, by use of a predetermined number (e.g., 100) of gas sensors 10, a reference time and a target range are determined, and a comparison table is formed. The reference time is the time of the preliminary control which is performed in order to determine the electric current supply time contained in the control conditions. When the relation between the change pattern and the electric current supply time in the preliminary control performed in the presence of the reference gas is compared among gas sensors 10 having the same configuration, in general, the gas sensors 10 show the tendency that the shorter the electric current supply time during the preliminary control, the larger the $NO_X$ concentration correspondence value immediately (e.g., 10 seconds) after the start of the drive control. For example, FIG. 3 exemplifies, for a gas sensor 10 having the above-described configuration, the relation between the change pattern and the electric current supply time during the preliminary control performed in the presence of the reference gas. Notably, in FIG. 3, the horizontal axis shows the time elapsed after the start of the drive control performed after the end of the preliminary control.

Figure 3:
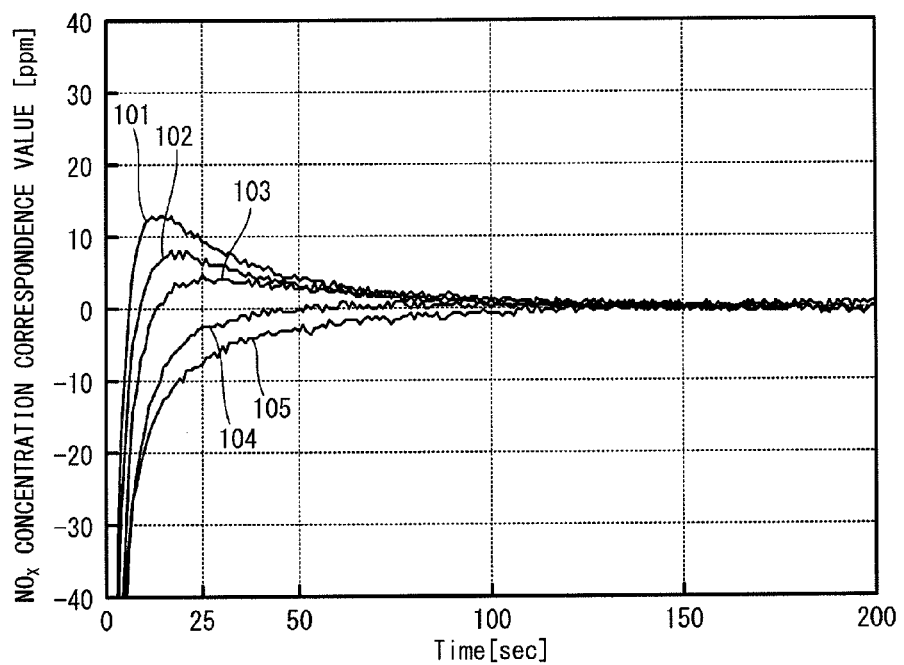
FIG. 3 is a graph showing time course changes in an $NO_X$ concentration correspondence value immediately after the start of drive control for the case where preliminary control was executed for the same gas sensor 10, while changing the time over which electric current was supplied thereto.

As shown in FIG. 3, the $NO_X$ concentration correspondence value after passage of 25 sec from the start of the drive control increases in the order of a change pattern 101 (electric current supply time: 8 sec), a change pattern 102 (electricity supply time: 9 sec), a change pattern 103 (electric current supply time: 10 sec), a change pattern 104 (electric current supply time: 20 sec), and a change pattern 105 (electric current supply time: 50 sec). Notably, the reference gas refers to as a gas whose $NO_X$ concentration is known. Since a determination is made as to whether or not the $NO_X$ concentration correspondence value falls within a predetermined target range (e.g., 0±5 ppm), preferably, the $NO_X$ concentration of the reference gas is 0 ppm. In the present embodiment, the composition of the reference gas was determined such that $NO_X$: 0 ppm; $O_2$: 7%, $H_2O$: 4%; and $N_2$ gas: balance. The temperature of the reference gas was set to 150° C.

Furthermore, although not illustrated, when the relation between the electric current supply time and variation in the $NO_X$ concentration correspondence value immediately after the start of the drive control is compared among a predetermined number of gas sensors 10, a tendency is found that the shorter the electric current supply time, the greater the variation. In particular, in the case where a short electric current supply time equal to or less than the reference time is set, the shorter the reference time, the greater the possibility that the variation in the electric current supply time among the gas sensors 10 increases, and the time required for the output of the gas sensor 10 to become stable increases. Accordingly, the reference time is determined in consideration of the variation among the gas sensors 10 and the time required for stabilizing the output. In the present embodiment, the reference time is set to 20 sec.

Figure 4:
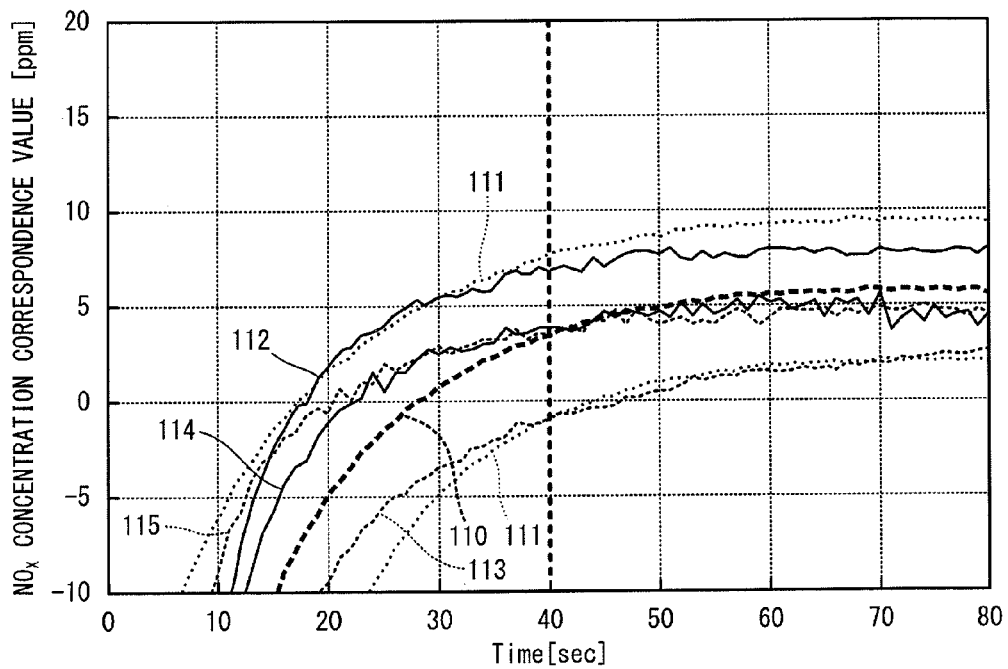
FIG. 4 is a graph showing time course changes in the $NO_X$ concentration correspondence value immediately after the start of drive control for the case where preliminary control of a reference time was performed.

The representative pattern 110 is determined through use of the predetermined number of gas sensors 10 as in the above-described case. Specifically, the preliminary control for supplying the constant current is performed in the presence of the reference gas, with the electric current supply time being set to the reference time (20 sec). A change pattern is obtained on the basis of the output of each gas sensor 10 immediately after the start of the drive control in the presence of the reference gas, and a change pattern exhibiting the most average tend (for example, a change pattern passing through the center of the range of variation) is defined as the representative pattern 110 as shown in FIG. 4. Furthermore, an appropriate range is determined with the representative pattern 110 being used as a reference, in consideration of the allowable range of variation of the $NO_X$ concentration correspondence value after the start of the drive control. The thus-determined range is used as a target range 111.

As described above, the shorter the electric current supply time during the preliminary control, the greater the $NO_X$ concentration correspondence value immediately after the start of the drive control. For example, a change pattern 112, which is shown in FIG. 4 as the output of a sample #1 (not shown) among a predetermined number of gas sensors 10, assumes a value larger than the representative pattern 110 at a point in time, for example, 40 sec after the start of the drive control. The change pattern 112 of the sample #1 can be rendered closer to the representative pattern 110 by rendering the electric current supply time during the preliminary control longer than the reference time. Similarly, a change pattern 113, which is shown in FIG. 4 as the output of a sample #2 (not shown) among the predetermined number of gas sensors 10, assumes a value smaller than the representative pattern 110 at the point in time 40 sec after the start of the drive control. The change pattern 113 of the sample #2 can be rendered closer to the representative pattern 110 by making the electric current supply time during the preliminary control shorter than the reference time.

Even when the electric current supply time during the preliminary control is adjusted in accordance with the individual difference of each gas sensor 10, a difficulty is encountered in obtaining a change pattern which completely coincides with the representative pattern 110. Therefore, in the present embodiment, an appropriate electric current supply time is set for each individual gas sensor 10 such that the change pattern after performing the preliminary control falls within the target range 111 determined on the basis of the representative pattern 110 (reference).

Figure 5:
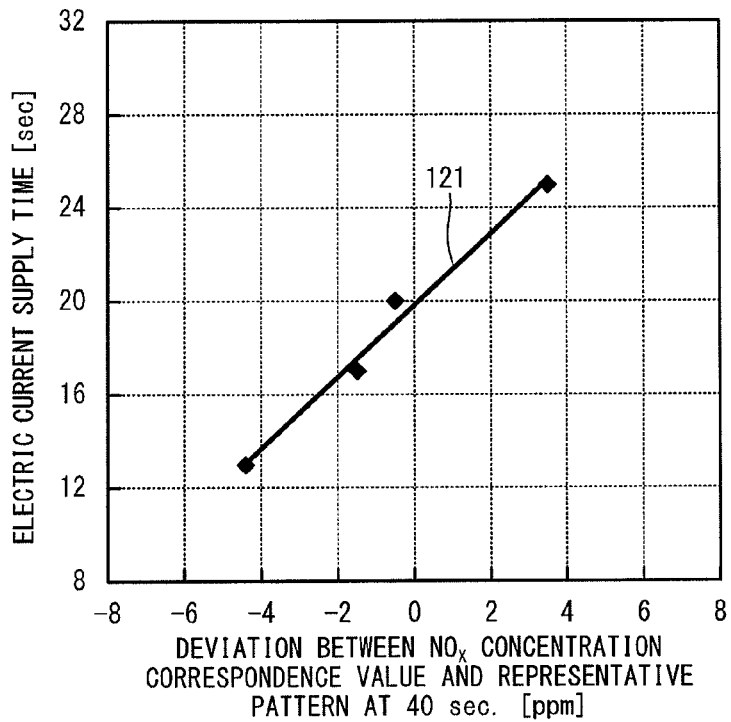
FIG. 5 is a graph showing the relation between the electric current supply time during the preliminary control and the deviation of the $NO_X$ concentration correspondence value from a representative pattern at a point 40 seconds after the start of drive control.

Such an appropriate electric current supply time is obtained from a graph shown in FIG. 5; that is, in accordance with the deviation of the $NO_X$ concentration correspondence value at the point in time 40 sec after the start of the drive control from the $NO_X$ concentration correspondence value of the representative pattern 110 at that point in time. Specifically, by means of properly changing the electric current supply time during the preliminary control, the electric current supply time is obtained in the case where the change pattern of the output of the gas sensor falls within the target range 111. Further, for that case, the deviation of the $NO_X$ concentration correspondence value is obtained at a point in time 40 sec after the start of the drive control from the $NO_X$ concentration correspondence value of the representative pattern 110 at that point in time. Similarly, the relation between the electric current supply time and the deviation is obtained for the predetermined number of gas sensors 10, and is plotted on the graph of FIG. 5. Then, a relational line 121, which shows the relation between the electric current supply time and the deviation, is obtained through use of, for example, the least-squares method. Notably, the reason why the deviation of the $NO_X$ concentration correspondence value is obtained at the point in time 40 sec after the start of the drive control is that such point is before a point in time by which the $NO_X$ concentration correspondence value becomes stable after the start of the drive control, and, at that point, the variation of the output value among the gas sensors 10 is large due to their individual differences.

Through use of the relational line 121 of the graph of FIG. 5, an optimal electric supply time during the preliminary control is obtained for each of the samples #1 and #2, which exhibit the respective change patterns 112 and 113 shown in FIG. 4. Change patterns 114 and 115 of FIG. 4 show respective change patterns of the outputs of the samples #1 and #2 for which the preliminary control was performed in accordance with the obtained electric supply time. As shown in FIG. 4, each of the change patterns 114 and 115 of the outputs of the samples #1 and #2 after the start of the drive control in the case where the preliminary control was performed in accordance with the electric supply time obtained by use of the relational line 121 of FIG. 5 falls within the target range 111 determined on the basis of the representative pattern 110.

As described above, as a result of the electric current supply time being adjusted on the basis of the reference time, the change pattern of the output of each gas sensor 10 falls within the target range 111 set on the basis of the representative pattern 110. That is, the trend of the change pattern becomes substantially the same as that of the representative pattern 110. Therefore, as described above, accurate measurement can be performed by obtaining the $NO_X$ concentration correspondence value after the output value of the gas sensor 10 becomes stable (after the fluctuation of the output value due to its time course change falls within a range of 0±5 ppm). In the present embodiment, the electric current supply time obtained for each individual gas sensor 10 in the above-described manner is stored in the EEPROM 66, and, in the main processing described below, the preliminary control is performed on the basis of the electric current supply time read from the EEPROM 66.

Incidentally, as a result of performing the preliminary control, the trend of the change pattern of the gas sensor 10 becomes substantially the same as that of the representative pattern 110. Therefore, if the output of the gas sensor 10 is corrected using the representative pattern 110, a corrected value (obtained by correcting the output value) can be rendered stable even before the original output value of the gas sensor 10 becomes stable. In the present embodiment, pattern data representing the representative pattern 110 is stored in the EEPROM 66 in advance as correction data common among a plurality of gas sensors 10 having the same structure.

Figure 6:
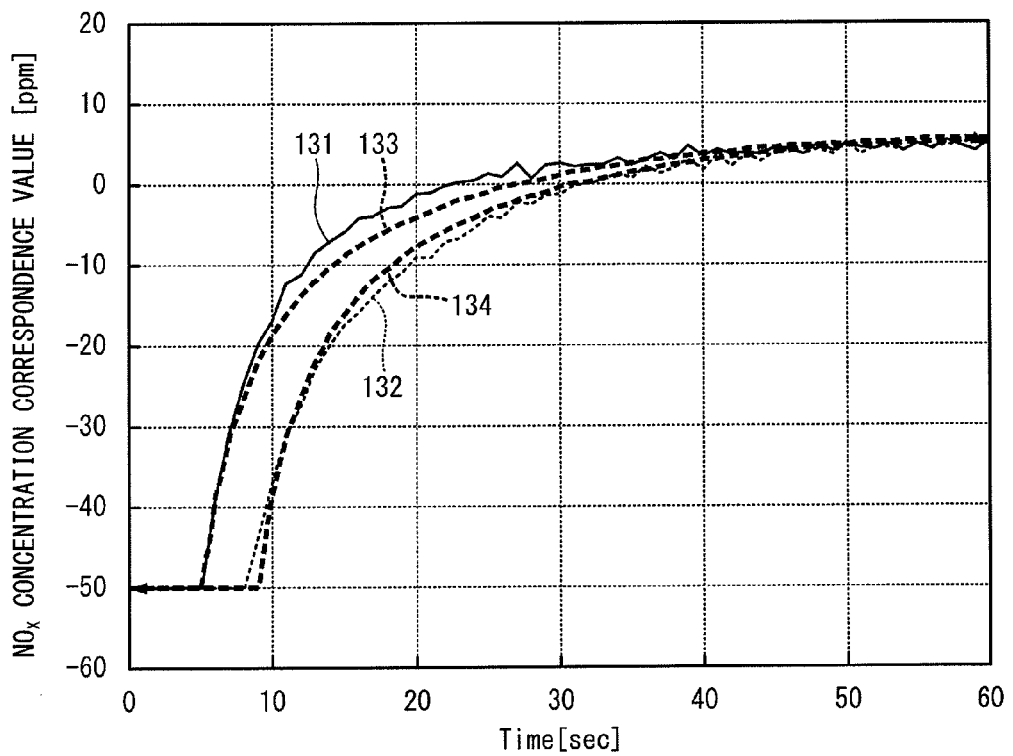
FIG. 6 is a graph showing time course changes in the $NO_X$ concentration correspondence value immediately after the start of drive control for the case where control conditions (electric current supply time) is set for each gas sensor 10.
Figure 7:
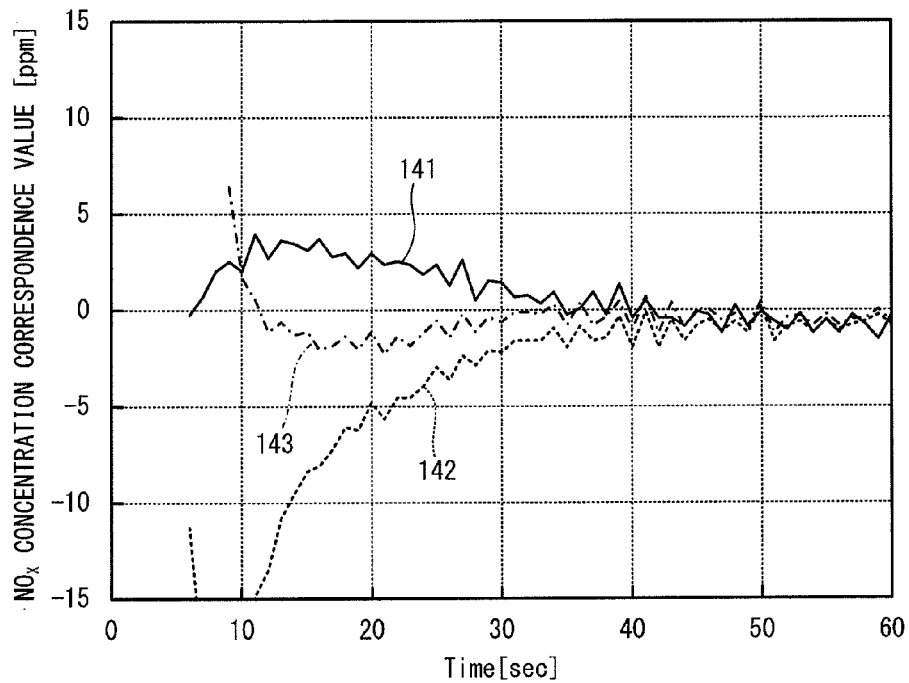
FIG. 7 is a graph showing, for comparison, a time course change in the case where the $NO_X$ concentration correspondence value immediately after the start of drive control is corrected and in the case where the $NO_X$ concentration correspondence value is not corrected.

A specific example will next be described. The graph of FIG. 6 shows the change pattern 131 of the output of sample #3 (not shown) among the predetermined number of gas sensors 10 in the presence of the reference gas. The trend of the time course change of the change pattern 131 is such that the output changes to follow a pattern 133 which exhibits the same trend as the representative pattern 110 (see FIG. 4). If the pattern 133 is the same as the representative pattern 110 (see FIG. 4), a corrected pattern 141 shown in FIG. 7 is obtained by correcting the change pattern 131 of the output of the sample #3 by making use of the representative pattern 110. The correction is performed in accordance with a formula (the corrected pattern 141)=(the change pattern 131 of the output of the sample #3)−(the representative pattern 110). Notably, the correction is performed by use of respective values obtained from the change pattern 131 and the representative pattern 110 for the same timing. As a result of correcting the output of the sample #3 as indicated by the corrected pattern 141, it becomes possible to obtain a stable $NO_X$ concentration correspondence value immediately after the start of the drive control; i.e., before the original output value of the gas sensor 10 becomes stable (for example, before elapse of 20 sec (see FIG. 6)).

However, even among a plurality of gas sensors 10 for which the electric current supply time during the preliminary control is set to the same period, a variation may be produced in the time (timing) at which the trend of the time course change appears at the beginning of the oxygen pumping back operation performed after the start of the drive control. This variation in timing is caused by difference in follow-up performance among the gas sensors 10. Specifically, when the mode of controlling the gas sensor 10 is switched from preliminary control to drive control, the direction and magnitude of the current supplied to the detection element 11 change, and the gas sensor 10 (the detection element 11) responds to follow the change. However, the follow-up performance varies among the gas sensors 10.

A specific example will be described. The graph of FIG. 6 shows the change pattern 132 of the output of the sample #4 (not shown) among the predetermined number of gas sensors 10 in the presence of the reference gas. The trend of the time course change of the change pattern 132 of the sample #4 is such that the output changes to follow a pattern 134 which exhibits the same trend as the representative pattern 110 (see FIG. 4) at a timing delayed from the change pattern 131 of the sample #3. If the pattern 132 of the sample #4 is corrected by use of the representative pattern 110, a corrected pattern 142 shown in FIG. 7 is obtained. The correction is performed in accordance with a formula (the corrected pattern 142)=(the change pattern 132 of the output of the sample #4)−(the representative pattern 110). As indicated by the corrected pattern 142, despite correcting the output of sample #4, a stable $NO_X$ concentration correspondence value cannot be obtained immediately after the start of the drive control. This is because the pattern 134 and the representative pattern 110 differ from each other in timing.

In order to solve such a problem, in the present embodiment, the timing at which the output value of the gas sensor 10 is corrected by use of the representative pattern 110 is adjusted in accordance with the individual characteristics of the gas sensor 10. A specific example will be described. When the change pattern 132 of the sample #4 among the gas sensors 10 is corrected by use of the above-mentioned pattern 134 (see FIG. 6) whose timing has been adjusted to coincide with the timing of the output of the sample #4, a corrected pattern 143 shown in FIG. 7 is obtained. Notably, the correction is performed in accordance with a formula (the corrected pattern 143)=(the change pattern 132 of the output of the sample #4)−(the pattern 134 exhibiting the same trend as the representative pattern 110). As indicated by the corrected pattern 143, when the output of the sample #4 is corrected by use of the pattern 134 at a proper timing, it becomes possible to obtain a sable $NO_X$ concentration correspondence value even before the original output value of the gas sensor 10 becomes stable, as in the above-described case.

Such correction using the representative pattern 110 is performed upon elapse of an application time set for each gas sensor 10 in advance. The application time refers to a timing at which the correction using the representative pattern 110 is performed and which is represented by a time measured from the end of the preliminary control; i.e., the start of the drive control. In the present embodiment, the above-described test using a reference gas is performed for each gas sensor 10, and the timing at which correction is to be performed is obtained as an application time and is stored in the EEPROM 66. Subsequently, the application time is read out in the main processing described below, and the processing of correcting the output of the gas sensor 10 is started upon elapse of the application time after the start of the drive control.

Next, the main processing of the present embodiment will be described with reference to FIGS. 2A and 2B. The CPU 61 executes the main processing upon receipt of an instruction from the ECU 90 at the time of startup of the internal combustion engine (not shown). Notably, the $NO_X$ concentration correspondence value calculated in the main processing is output to the ECU 90 of the sensor control apparatus 5, at predetermined intervals, in output processing executed separately from the main processing, when the application time is determined to have elapsed after the start of the drive control. Notably, in the output processing, the outputting of the $NO_X$ concentration correspondence value may be started immediately after the elapse of the application time or may be started after a predetermined time elapses after the elapse of the application time.

When the internal combustion engine (not shown) is started and an instruction is fed from the ECU 90 to the signal input/output section 64, the CPU 61 obtains from the ROM 63 and the EEPROM 66 parameters and various conditions for executing the main processing (S5). In S5, for example, the electric current supply time during the preliminary control set for each gas sensor 10 is read out of the EEPROM 66. The above-mentioned application time is read from the EEPROM 66 as timing for performing the correction using the representative pattern 110. Next, the CPU 61 executes the activation processing (S10 to S30). In the activation processing, the CPU 61 starts the supply of electric current to the heater conductor 38 of the gas sensor 10 (S10). Specifically, the CPU 61 applies a constant voltage (e.g., 12 V) to the heater conductor 38 by controlling the heater drive circuit 59.

Next, the CPU 61 starts the supply of the current Icp to the Vs cell 3 by controlling the Icp supply circuit 54 (S15). The Vs cell 3 supplied with the current Icp pumps oxygen from the first measurement chamber 23 into the reference oxygen chamber 29. As the internal resistance of the Vs cell 3 decreases as a result of the detection element 11 being heated by the heater element 35, the voltage Vs of the Vs cell 3 decreases gradually.

Next, the CPU 61 determines whether or not the voltage Vs obtained via the Vs detection circuit 53 is equal to or less than a predetermined value Vth (S20). When the voltage Vs is not equal to or less than the predetermined value Vth (S20: NO), the CPU 61 waits until the voltage Vs becomes equal to or less than the predetermined value Vth. When the voltage Vs is equal to or less than the predetermined value Vth (S20: YES), the CPU 61 starts to control the heater voltage Vh (S25). Specifically, the CPU 61 controls the supply of electric current to the heater element 35 via the heater drive circuit 59 such that the internal resistance Rpvs of the Vs cell 3 becomes equal to a target value. The target value is 300Ω, for example. When the internal resistance Rpvs is 300Ω, the temperature of the Vs cell 3 is estimated to be about 750° C.

Next, the CPU 61 determines whether or not the detection element 11 has been activated (S30). Specifically, the CPU 61 determines whether or not the detection element 11 has been activated, by determining whether or not the internal resistance Rpvs of the Vs cell 3 has reached a threshold value. The internal resistance Rpvs of the Vs cell 3 is calculated on the basis of the amount of change in the voltage Vs obtained via the resistance detection circuit 55, and a table which represents the previously determined relation between the amount of change in the voltage Vs and the internal resistance of the Vs cell 3. The threshold value is 350Ω, for example. When the internal resistance Rpvs is 350Ω, the temperature of the Vs cell 3 is estimated to be about 650° C. When the internal resistance Rpvs has reached the threshold, the CPU 61 determines that the detection element 11 has become activated.

When the detection element 11 has not yet become activated (S30: NO), the CPU 61 waits until the detection element 11 becomes activated. When the detection element 11 has become activated (S30: YES), the CPU 61 causes the Ip1 drive circuit 52 to operate, to thereby start the supply of electric current to the Ip1 cell 2 (S35). The supply of electric current to the Ip1 cell 2 is performed so as to adjust the oxygen concentration of the exhaust gas introduced into the first measurement chamber 23 to the predetermined concentration C.

Next, the CPU 61 executes the preliminary control processing (S40 to S50). In the preliminary control processing, the CPU 61 supplies a constant current to the Ip2 cell 4 over a constant electric current supply time set for each gas sensor 10 (S40). Specifically, the CPU 61 causes the constant current circuit 58 to operate, to thereby supply the constant current Ip3 to the Ip2 cell 4. In the present embodiment, the constant current Ip3 is 10 μA. Upon receipt of the current Ip3, the Ip2 cell 4 starts to pump oxygen out of the second measurement chamber 30.

Next, the CPU 61 executes timer processing for counting the elapsed time (S45). The timer processing is processing executed separately from the main processing. In the timer processing, a count value is increased by an increment every time a predetermined period of time elapses. The increased count value is stored in the RAM 62. Next, the CPU 61 determines whether the electric current supply time has elapsed by determining whether or not the count value stored in the RAM 62 has reached a value corresponding to the electricity supply time (S50). In the case where the electric current supply time has not yet elapsed, the CPU 61 waits (S50: NO). In the case where the electric current supply time has elapsed (S50: YES), the CPU 61 ends the preliminary control processing, and switches the control of the Ip2 cell 4 to the drive control (S55). The CPU 61 stops operation of the constant current circuit 58, and causes the Vp2 application circuit 57 to operate, to thereby switch the control state of the sensor control apparatus 5 from preliminary control to drive control. In the drive control, the operating voltage Vp2 (e.g., 450 mV) is applied to the Ip2 cell 4. In the drive control, the control for supplying electric current to the Ip1 cell 2, which was started in S35, is executed continuously.

Next, the CPU 61 again executes the above-described timer processing (S57). That is, the CPU 61 resets the count value to zero, increases the count value by the increment at predetermined time intervals, and stores it in the RAM 62. Subsequently, the CPU 61 obtains the value of the current Ip2 detected by the Ip2 detection circuit 56 (more specifically, a voltage obtained from the current Ip2 through current-voltage conversion), and stores in the RAM 62 the obtained value of the current Ip2 and the count value at the time of obtainment (S60).

Next, the CPU 61 determines whether or not the application time has elapsed by determining whether or not the count value stored in the RAM 62 by the timer processing has reached a value corresponding to the application time (S65). In the case where the application time has not yet elapsed (S65: NO), the CPU 61 returns to S60, obtains the value of the current Ip2 and the count value, and stores them in the RAM 62. In the case where the application time has elapsed (S65: YES), the CPU 61 calculates the $NO_X$ concentration correspondence value on the basis of the value of the Ip2 stored in the RAM 62, and stores the calculated $NO_X$ concentration correspondence value in the RAM 62 (S70). The $NO_X$ concentration correspondence value is calculated by, for example, applying the value of the current Ip2 to a predetermined formula stored in the ROM 63. Alternatively, with reference to a table which represents the relation between the value of the current Ip2 and the $NO_X$ concentration correspondence value, an $NO_X$ concentration correspondence value corresponding to the value of the current Ip2 obtained in S60 is calculated.

Next, the CPU 61 determines whether or not the correction time has elapsed by determining whether the count value stored in the RAM 62 by the timer processing has reached a value corresponding to the correction time (S65). In the case where the correction time has not yet elapsed (S72: NO), the CPU 61 corrects the $NO_X$ concentration correspondence value calculated in S70, and stores (overwrites) the corrected $NO_X$ concentration correspondence value in the RAM 62 (S75). Notably, the $NO_X$ concentration correspondence value is corrected in accordance with a formula (the corrected $NO_X$ concentration correspondence value)=(the $NO_X$ concentration correspondence value calculated in S70)−(correction data based on the representative pattern 110). The correction data stored in the EEPROM 66 are applied to the above-described formula. Specifically, when the count value increased by the timer processing reaches a value corresponding to the application time, an operation of reading out the correction data is started so that the data are read out in synchronism with the count value, and the read data are applied to the formula.

Next, when an end instruction is not received from the ECU 90 (S80: NO), the CPU 61 returns to S60. In the case where the correction time has elapsed while S60 to S75 are repeated (S72: YES), after that point in time, the CPU 61 proceeds from S72 to S80. Therefore, correction of the $NO_X$ concentration correspondence value calculated in S70 is not performed. When an end instruction is received from the ECU 90 (S80: YES), the CPU 61 ends the main processing.

Notably, the present invention is not limited to the above-described embodiment, and the embodiment may be modified in various ways without departing from the scope of the invention. In the above-described embodiment, an $NO_X$ sensor for detecting the concentration of $NO_X$ is exemplified as a gas sensor 10. However, the present invention can be applied to various gas sensors constituted by solid electrolyte bodies (e.g., an oxygen sensor).

Also, the configuration of the sensor control apparatus 5 may be freely changed. For example, the configuration of the drive circuit section 50 may be freely changed. Moreover, the sensor control apparatus 5 and the gas sensor 10 may be unitarily assembled. Also, the sensor control apparatus 5 may be applied to control of a gas sensor which includes an atmospheric-air introduction hole in place of the reference oxygen chamber 29. The control conditions, the application time, the correction time, and the correction data stored in the EEPROM 66 may be stored in any storage device (other than the EEPROM 66), such as the ROM 63, of the sensor control apparatus 5. Needless to say, the above-described embodiment may be modified such that the control conditions, the application time, and the correction time are stored in the EEPROM 66 and the correction data are stored in the ROM 63. That is, the type of the storage device and the location of the storage device may be freely changed. Also, the above-described embodiment may be modified such that a storage device is provided, for example, in the connector section 40 of the gas sensor 10, and the control conditions, the application time and the correction time are stored in the storage device. Alternatively, the above-described embodiment may be modified such that a fixed resistor is provided in the gas sensor 10, and the ROM 63 stores a table which defines the correlation between the resistance of the fixed resistor and at least one of the control conditions, the application time and the correction time. In this case, in the main processing, the resistance of the fixed resistor is read in S5, and at least one of the control conditions, the application time and the correction time which corresponds to the resistance is read with reference to the table.

The control conditions may be freely changed. In the present embodiment, the electric current supply time during the preliminary control is set for each gas sensor 10 as the control conditions. The control conditions are not limited thereto, and the control conditions may be set so that the electric current supply time at the time of the preliminary control is set, as common control conditions, for all the gas sensors 10, and the value of the constant current is set for each gas sensor 10. In this case, in the main processing shown in FIGS. 2A and 2B, the processing of S41 to S51 shown in FIG. 8 may be executed in place of the processing of S40 to S50 executed as the preliminary control.

Figure 2B:
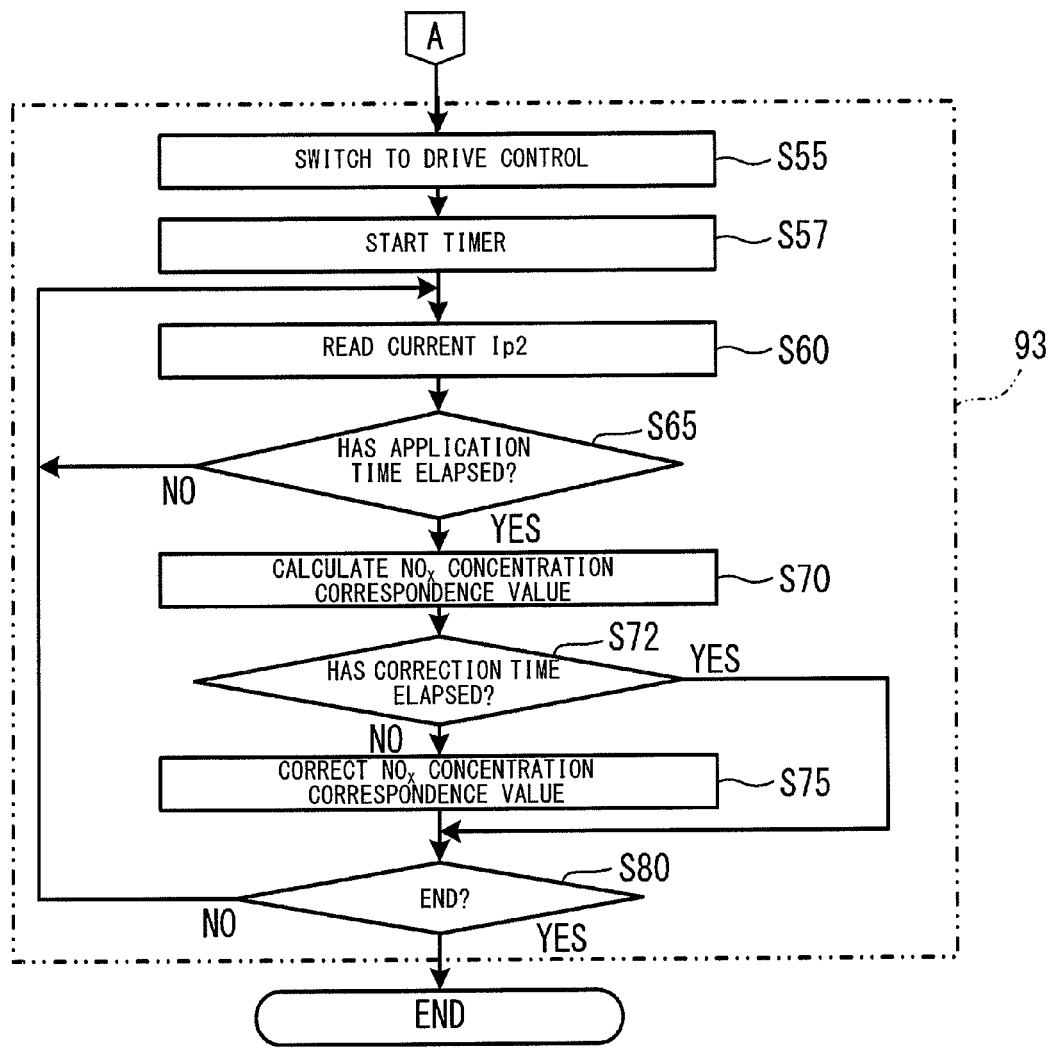
Figure 8:
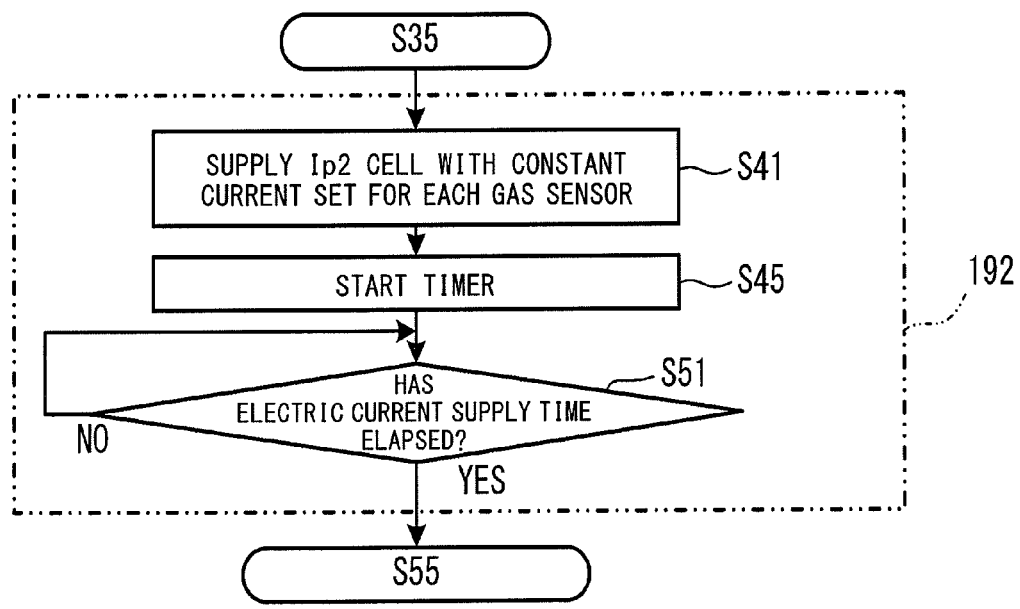
FIG. 8 is a flowchart showing a modification of preliminary control processing.

In FIG. 8, steps identical to the steps of the main processing of FIGS. 2A and 2B are denoted by the same step numbers. The main processing of FIG. 8 differs from the main processing of FIGS. 2A and 2B in S41 and S51 of the preliminary control processing within a two-dot chain line 192. Description of the steps of the main processing of FIG. 8 similar to those of the main processing of FIGS. 2A and 2B will be omitted. When the supply of electric current to the Ip1 cell 2 is started in S35 after completion of the activation processing of the main processing, in S41, the CPU 61 supplies to the Ip2 cell 4 the constant current set for each gas sensor 10. The CPU 61 starts the timer processing in S45, and waits in S51 until the electric current supply time common among the gas sensors 10 elapses (S51: NO). When the electric current supply time has elapsed (S51: YES), the CPU 61 proceeds to S55, and executes the drive control processing.

Notably, the constant current set for each gas sensor 10 may be obtained in the same manner as in the above-described embodiment. That is, a predetermined number of gas sensors 10 are prepared. Preliminary control for supplying a constant current set to a reference value (e.g., 10 µA) for a certain time (e.g., 20 sec) is performed for each gas sensor 10 in the presence of the reference gas so as to determine the representative pattern 110, and the target range 111 is then set. Furthermore, the preliminary control is performed for the predetermined number of gas sensors 10 while the constant current supplied during the preliminary control is changed appropriately, and the constant current is obtained in the case where the change pattern of the output of the gas sensor 10 falls within the target range 111. Subsequently, the deviation between the NO$_X$ concentration correspondence value is obtained at a point in time 40 sec after the start of the drive control in the case where the change pattern of the output of the gas sensor 10 falls within the target range 111, and the NO$_X$ concentration correspondence value of the representative pattern 110 at that point in time. Subsequently, a graph is made which is similar to that shown in FIG. 5 and which represents the relation between the constant current and the deviation. A proper constant current is set for each gas sensor 10 such that the change pattern of the output of the gas sensor 10 falls within the target range 111 determined on the basis of the representative pattern 110.

Needless to say, the electric current supply time and the constant current (control conditions) at the time of the preliminary control may be set for each gas sensor 10. Alternatively, the control conditions may be set as conditions common among the gas sensors 10.

Also, the main processing may be freely changed. For example, the processing of correcting the NO$_X$ concentration correspondence value by use of correction data in S75 of FIG. 2B may be modified such that it does not end upon elapse of the correction time but is executed over the entire period during which the drive control is executed. Alternatively, the processing of S75 may be modified such that the fluctuation of the NO$_X$ concentration correspondence value before being corrected is checked, and the processing of S75 is ended when a state in which the fluctuation falls within a predetermined range continues over a predetermined time.

The target range may be any range which is properly determined in consideration of an allowable range of variation of the concentration correspondence value after the start of the drive control, and the setting method may be freely changed. For example, in the above-described embodiment, the target range is a predetermined range set on the basis of the representative pattern 110 (reference). However, the method of setting the target range is not limited thereto, and the target range may be determined on the basis of a range of the NO$_X$ concentration correspondence value after elapse of a predetermined time (e.g., 20 sec) after the start of the drive control.

Furthermore, in the above-described embodiment, the operation of correcting the NO$_X$ concentration correspondence value by making use of the representative pattern 110 is performed after elapse of the application time from the start of the drive control. However, the application time is not necessarily required to be set in advance. In this case, the process of S65 may be modified such that the CPU 61 obtains a differentiated value of the output value of the gas sensor 10, and compares it with a differentiated value of the representative pattern 110 at a predetermined timing or a predetermined threshold. When the obtained differentiated value does not coincide with that of the representative pattern 110 or the threshold, the CPU 61 returns to S60. When the obtained differentiated value coincides with that of the representative pattern 110 or the threshold, the CPU 61 proceeds to S70, and performs correction by making use of the representative pattern 110. Moreover, if the above-mentioned differentiated value is obtained from the output value of the gas sensor 10 after noise is removed from the output value by a known method, the timing at which correction is started can be determined more accurately. In this case, the CPU 61, which obtains the differentiated value of the output value of the gas sensor 10, compares it with a differentiated value of the representative pattern 110 at the predetermined timing or the predetermined threshold, and performs the correction by making use of the representative pattern 110 when the differentiated value coincides with the differentiated value of the representative pattern 110 or the threshold, corresponding to the "determination means" of claims.

Notably, in the present invention, the solid electrolyte body 12 corresponds to the "first solid electrolyte layer"; and the electrodes 17 and 18 correspond to the "paired first electrodes." The solid electrolyte body 14 corresponds to the "second solid electrolyte layer"; and the electrodes 27 and 28 correspond to the "paired second electrodes." The Ip1 cell 2 corresponds to the "first oxygen pump cell"; and the Ip2 cell 4 corresponds to the "second oxygen pump cell." The EEPROM 66 corresponds to the "storage means."

The CPU 61, which switches the control for the Ip2 cell 4 to the drive control in S55, corresponds to the "drive control means." The CPU 61, which performs the preliminary control in S40 so as to supply a constant current to the Ip2 cell 4 for a constant electric current supply time, corresponds to the "preliminary control means." The CPU 61, which calculates the $NO_X$ concentration correspondence value on the basis of the current Ip2 in S70, corresponds to the "calculation means." The CPU 61, which determines in S65 whether or not the application time has elapsed, corresponds to the "determination means." The CPU 61, which in S75 corrects the $NO_X$ concentration correspondence value calculated in S70, corresponds to the "correction means."

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-54979 filed Mar. 14, 2011, the disclosure of which is incorporated herein by reference in its entirety.

What is claimed is:

1. A sensor control apparatus for controlling a gas sensor including a first measurement chamber into which an object gas is introduced, a first oxygen pump cell having a first solid electrolyte layer and paired first electrodes provided on an inside and outside, respectively, of the first measurement chamber, a second measurement chamber in communication with the first measurement chamber, and a second oxygen pump cell having a second solid electrolyte layer and paired second electrodes provided on an inside and outside, respectively, of the second measurement chamber, the sensor control apparatus comprising:

a drive control section programmed to perform drive control for adjusting an oxygen concentration of the object gas introduced into the first measurement chamber by supplying an electric current to the first oxygen pump cell and for applying an operating voltage to the second oxygen pump cell;

a preliminary control section programmed to perform, before start of the drive control, preliminary control which supplies a constant current to the second oxygen pump cell over a constant period of time, to thereby control to a constant level an amount of oxygen pumped out from the second measurement chamber to outside of the second measurement chamber;

a calculation section programmed to calculate a concentration correspondence value which represents a concentration of a specific gas contained in the object gas, on the basis of the magnitude of current flowing through the second oxygen pump cell to which the operating voltage is applied after the start of the drive control;

a storage medium for storing, as correction data common among a plurality of the gas sensors, pattern data which represents a pattern of a time course change in the concentration correspondence value after the drive control is started after the preliminary control which has been set in advance is executed, which pattern data is obtained under a condition where both the preliminary control and the drive control are performed in the presence of a reference gas;

a determination section programmed to determine a timing for applying the correction data; and a correction section programmed to correct the concentration correspondence value by applying the correction data to the concentration correspondence value at the timing determined by the determination means, said correction data being applied when the determination section determines that a pattern of a time course change exhibited by the concentration correspondence value after the start of the drive control approximately coincides with the pattern of the time course change represented by the correction data.

2. The sensor control apparatus as claimed in claim 1, wherein the storage medium stores an application time which is determined for the gas sensor on an individual basis and represents a time between the start of the drive control and the timing for applying the correction data, the application time being used to apply the correction data such that the pattern of the time course change in the concentration correspondence value after the drive control is started after execution of the preliminary control, both controls being performed in the presence of the reference gas, approximately coincides with the pattern of the time course change represented by the correction data; and the determination means determines that the timing for applying the correction data has come when the application time elapses after the start of the drive control.

3. The sensor control apparatus as claimed in claim 1, wherein the storage medium further stores control conditions of the sensor control apparatus which are determined for the gas sensor on an individual basis and which relate to adjustment of the amount of pumped out oxygen, the control conditions being determined such that the concentration correspondence value after the drive control is started after execution of the preliminary control, both controls being performed in the presence of the reference gas, falls within a target range; and the preliminary control section executes the preliminary control under the control conditions.

4. The sensor control apparatus as claimed in claim 3, wherein the control conditions include at least one of constant current and constant time determined for the gas sensor on an individual basis.

5. A sensor control system comprising a gas sensor and a sensor control apparatus as claimed in claim 1, wherein the gas sensor is controlled by the sensor control apparatus.

6. A sensor control method which is performed in a sensor control apparatus for controlling a gas sensor including a first measurement chamber into which an object gas is introduced, a first oxygen pump cell having a first solid electrolyte layer and paired first electrodes provided on an inside and outside, respectively, of the first measurement chamber, a second measurement chamber in communication with the first measurement chamber, and a second oxygen pump cell having a second solid electrolyte layer and paired second electrodes provided on an inside and outside, respectively, of the second measurement chamber, the sensor control method comprising:

a drive control step of performing drive control for adjusting an oxygen concentration of the object gas introduced into the first measurement chamber by supplying electric current to the first oxygen pump cell and for applying an operating voltage to the second oxygen pump cell;

a preliminary control step of performing, before start of the drive control, preliminary control which supplies a constant current to the second oxygen pump cell over a constant period of time, to thereby control to a constant level an amount of oxygen pumped out from the second measurement chamber to the outside of the second measurement chamber;

a calculation step of calculating a concentration correspondence value which represents a concentration of a specific gas contained in the object gas, on the basis of the magnitude of current flowing through the second oxygen pump cell to which the operating voltage is applied after the start of the drive control;

a determination step of determining a timing for applying correction data, such that a pattern of a time course change exhibited by the concentration correspondence value after the start of the drive control approximately coincides with a pattern of a time course change represented by the correction data, the correction data being pattern data which is stored in storage means of the sensor control apparatus commonly among a plurality of the gas sensors and which represents a pattern of a time course change in the concentration correspondence value after the drive control is started after the preliminary control which has been set in advance is executed, which pattern data is obtained under a combination where both the preliminary control and the drive control are performed in the presence of the reference gas; and a correction step of correcting the concentration correspondence value by applying the correction data to the concentration correspondence value on the basis of the timing determined by the determination step.

7. A sensor control method as claimed in claim 6, wherein the storage means stores an application time which is individually determined for the gas sensor and represents a time between the start of the drive control and the timing for applying the correction data, the application time being used to apply the correction data such that the pattern of the time course change in the concentration correspondence value after the drive control is started after execution of the preliminary control, both controls being performed in the presence of the reference gas, approximately coincides with the pattern of the time course change represented by the correction data; and the determination step determines that the timing for applying the correction data has come when the application time elapses after the start of the drive control.

* * * * *